United States Patent
Tyber (10) Patent No.: US 10,201,433 B2
(45) Date of Patent: Feb. 12, 2019

(54) SYSTEM AND METHOD FOR CORRECTING SCOLIOSIS

(71) Applicant: Tyber Medical LLC, Bethlehem, PA (US)

(72) Inventor: Jeffrey Tyber, Landing, NJ (US)

(73) Assignee: Tyber Medical LLC, Bethlehem, PA (US)

(*) Notice: Subject to any disclaimer, the term of this patent is extended or adjusted under 35 U.S.C. 154(b) by 422 days.

(21) Appl. No.: 14/948,322

(22) Filed: Nov. 22, 2015

(65) Prior Publication Data
US 2016/0128844 A1    May 12, 2016

Related U.S. Application Data (63) Continuation-in-part of application No. 14/513,300, filed on Oct. 14, 2014, which is a continuation-in-part
(Continued)

(51) Int. Cl.
*A61F 2/44*    (2006.01)
*A61B 17/80*    (2006.01)
(Continued)

(52) U.S. Cl.
CPC .......... *A61F 2/447* (2013.01); *A61B 17/8095* (2013.01); *A61B 90/94* (2016.02);
(Continued)

(58) Field of Classification Search
CPC ..................... A61F 2/44–2002/4495
See application file for complete search history.

(56) References Cited

U.S. PATENT DOCUMENTS 5,152,791 A * 10/1992 Hakamatsuka ........... A61F 2/28
                                                         623/23.56
5,888,227 A *  3/1999 Cottle ..................... A61F 2/442
                                                         623/17.16
(Continued)

FOREIGN PATENT DOCUMENTS

WO    WO2007098288    8/2007

OTHER PUBLICATIONS

International Search Report and Written Opinion for PCT/US2014/060338, dated Jan. 19, 2015. 16 pages.
(Continued)

*Primary Examiner* — Zade Coley
(74) *Attorney, Agent, or Firm* — Joseph E. Maenner; Maenner & Associates, LLC (57) ABSTRACT

In described embodiments, an implant has an outer perimeter. The implant includes a top surface extending generally in a first plane and a bottom surface extending in a second plane. The second plane extends obliquely with respect to the first plane. The first plane intersects the second plane outside the outer perimeter of the implant. A medial surface extends between the top surface and the bottom surface proximate to the intersection of the first plane and the second plane. A lateral surface extends between the top surface and the bottom surface distal from the intersection of the first plane and the second plane. An anterior surface extends a first distance between the top surface and the bottom surface between the medial surface and the lateral surface. A posterior surface extends a second distance between the top surface and the bottom surface between the medial surface and the lateral surface. The second distance is greater than the first distance.

10 Claims, 12 Drawing Sheets

Related U.S. Application Data of application No. 14/054,100, filed on Oct. 15, 2013, now Pat. No. 9,387,087.

(60) Provisional application No. 61/715,891, filed on Oct. 19, 2012.

(51) Int. Cl.

| | | |
|---|---|---|
| *A61F 2/46* | (2006.01) | |
| *A61B 90/94* | (2016.01) | |
| *A61F 2/28* | (2006.01) | |
| *A61F 2/30* | (2006.01) | |
| *A61B 17/70* | (2006.01) | |
| *A61B 17/86* | (2006.01) | |
| *A61B 90/00* | (2016.01) | |

(52) U.S. Cl.
CPC .............. *A61F 2/28* (2013.01); *A61F 2/4455* (2013.01); *A61F 2/4465* (2013.01); *A61F 2/4603* (2013.01); *A61F 2/4611* (2013.01); A61B 17/7059 (2013.01); A61B 17/8645 (2013.01); A61B 2090/037 (2016.02); A61F 2/30771 (2013.01); A61F 2002/2817 (2013.01); A61F 2002/2835 (2013.01); A61F 2002/3008 (2013.01); A61F 2002/30013 (2013.01); A61F 2002/30029 (2013.01); A61F 2002/3082 (2013.01); A61F 2002/3092 (2013.01); A61F 2002/3093 (2013.01); A61F 2002/30266 (2013.01); A61F 2002/30281 (2013.01); A61F 2002/30321 (2013.01); A61F 2002/30326 (2013.01); A61F 2002/30355 (2013.01); A61F 2002/30509 (2013.01); A61F 2002/30578 (2013.01); A61F 2002/30714 (2013.01); A61F 2002/30774 (2013.01); A61F 2002/30808 (2013.01); A61F 2002/30836 (2013.01); A61F 2002/30843 (2013.01); A61F 2002/4475 (2013.01); A61F 2002/4623 (2013.01); A61F 2002/4627 (2013.01); A61F 2310/00407 (2013.01); A61F 2310/00461 (2013.01); A61F 2310/00796 (2013.01)

(56) References Cited

U.S. PATENT DOCUMENTS

| | | | |
|---|---|---|---|
| 6,261,291 B1 | 7/2001 | Talaber et al. | |
| 6,306,170 B2 | 10/2001 | Ray | |
| 6,623,484 B2 | 9/2003 | Betz et al. | |
| 6,790,233 B2* | 9/2004 | Brodke ............... | A61F 2/30767 623/17.11 |
| 7,238,203 B2* | 7/2007 | Bagga .................. | A61F 2/4455 623/17.11 |
| 7,641,690 B2 | 1/2010 | Abdou | |
| 8,216,312 B2 | 7/2012 | Gray | |
| 8,506,636 B2* | 8/2013 | Dye ...................... | A61F 2/4465 623/17.11 |
| 8,556,972 B2* | 10/2013 | Gordon ............... | A61F 2/30756 623/16.11 |
| 9,788,967 B2* | 10/2017 | Jo ......................... | A61F 2/4455 |
| 2004/0243241 A1* | 12/2004 | Istephanous ....... | A61B 17/7049 623/17.14 |
| 2005/0101960 A1 | 5/2005 | Fiere et al. | |
| 2006/0116766 A1* | 6/2006 | Lemaire ............... | A61F 2/447 623/17.11 |
| 2007/0270844 A1* | 11/2007 | Lin ....................... | A61F 2/4455 606/279 |
| 2008/0230421 A1 | 9/2008 | Pleil et al. | |
| 2008/0243135 A1 | 10/2008 | Robinson | |
| 2009/0182430 A1 | 7/2009 | Tyber et al. | |
| 2010/0152853 A1* | 6/2010 | Kirschman ............ | A61F 2/447 623/17.11 |
| 2011/0106171 A1 | 5/2011 | Kirschman | |
| 2011/0172780 A1 | 7/2011 | Scheland | |
| 2011/0224734 A1 | 9/2011 | Schelling | |
| 2012/0290091 A1* | 11/2012 | Kirschman ............ | A61F 2/447 623/17.16 |
| 2013/0238095 A1 | 9/2013 | Pavento et al. | |
| 2013/0268080 A1 | 10/2013 | Melkent et al. | |
| 2016/0151167 A1* | 6/2016 | Jo ......................... | A61F 2/4455 623/17.16 |
| 2016/0310286 A1* | 10/2016 | McJunkin .............. | A61F 2/441 |

OTHER PUBLICATIONS

Office Action for U.S. Appl. No. 14/054,100, dated Oct. 23, 2015.

\* cited by examiner

SYSTEM AND METHOD FOR CORRECTING SCOLIOSIS

CROSS-REFERENCE TO RELATED APPLICATIONS

This is a continuation-in-part of application Ser. No. 14/513,300, filed on Oct. 14, 2014, which is a Continuation-in-Part application of U.S. patent application Ser. No. 14/054,100, filed on Oct. 15, 2013, which claims priority from U.S. Provisional Patent Application Ser. No. 61/715,891, filed on Oct. 19, 2012, all of which are incorporated by reference herein in their entireties.

BACKGROUND OF THE INVENTION

Field of the Invention

The present invention relates to the treatment of scoliosis, and, in particular, to implant devices and methods for treating scoliosis.

Description of the Related Art

Treatment of scoliosis, which is a spinal deformity resulting in an abnormal curvature of the spine, can range from halo traction devices that severely limit the movement of the patient, to rod-based and interbody systems that are inserted along the spine. Both of these exemplary methods can be extremely traumatic to the patient.

Surgical attempts to correct curvatures of the spine were first attempted in the mid to late 19th century by using percutaneous myotomies of the vertebral musculature in addition to bracing. Further developments in the surgical aspects of correcting scoliosis were not realized until the early 1900s, but the development of external casts and braces continued throughout the late nineteenth century. For example, Plaster of Paris casts in 1880 were applied to patients while standing in vertical suspension devices. The bracing method tried to correct the deformity in both lateral and rotational methods and held them with a cast. Horizontal distraction frames utilized cast application to create a three-point fixation.

Later, postoperative immobilization such as the localizer cast, which consisted of a specialized frame where pressure was applied to the rib cage, was used. This allowed correction to be obtained immediately after surgery and also allowed for patients to be ambulatory after the operation. A Milwaukee brace was used initially as a postoperative immobilization device as well as a non-operative treatment of the disorder.

Further techniques used Harrington distraction instrumentation, which straightened the spine while holding the spinal column rigid while fusion took place. This included a steel rod on a ratchet system attached to the spine with hooks at the top and bottom of the curvature that would distract the curve when cranked. A segmental instrumentation system used crosslinking of two rods in the back to provide three-dimensional correction of the scoliotic deformity and decrease the need for immobilization after the surgery.

Presently, surgical practice uses a combination of devices (rods, cables, interbody cages, screws, and hooks) to move the spine into a natural alignment and keep it in that alignment until the bone graft fuses into place. These procedures generally link multiple vertebral bodies by attaching polyaxial screws or hooks to the spine and placing a rigid rod in place to link the spinal column. These procedures are completed with either an interbody fusion techniques or by leaving the native intervertebral disc intact.

However, hardware failure and non-fusion rates of 70% of patients receiving rod and screw fixation for multiple level deformity correction have been reported. The high degree of hardware failure suggests that alternative methods should be developed to both correct scoliosis deformity and minimize the reoperation rates.

Another alternative surgical method presently available approaches the lateral aspect of the spinal column through a lateral approach. Lateral interbody fusion has recently become attractive and a less invasive alternative to full posterior rod and screw fixation. The lateral procedure generally involves creating a lateral incision in the thoracolumbar spine, removing one or multiple intervertebral discs, and placing an intervertebral interbody spacer in place of the disc. The intervertebral interbodies are designed to realign the spine by including a built-in lordotic angle into the interbody. This procedure is commonly used in conjunction with lateral plating or in some instance posterior fixation with screws and rod fixation.

One major limitation with the interbody fusion technique is a surgeon's ability to correct only one plane of correction. Spinal scoliosis often involves multiple planes of deformity and requires correction of both sagittal alignment and coronal planes. The current interbody techniques on the market are only able to gain this correction in one plane and require additional alignment correction.

It would be beneficial to provide an implant that can be tailored to a single vertebra based on the particular physical needs of individual patients.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is an implant having an outer perimeter. The implant includes a top surface extending generally in a first plane and a bottom surface extending in a second plane. The second plane extends obliquely with respect to the first plane. The first plane intersects the second plane outside the outer perimeter of the implant. A medial surface extends between the top surface and the bottom surface proximate to the intersection of the first plane and the second plane. A lateral surface extends between the top surface and the bottom surface distal from the intersection of the first plane and the second plane. An anterior surface extends a first distance between the top surface and the bottom surface between the medial surface and the lateral surface. A posterior surface extends a second distance between the top surface and the bottom surface between the medial surface and the lateral surface. The second distance is greater than the first distance.

In an alternative embodiment, the present invention is a bi-planar adjustable implant comprising a body having a top surface, a bottom surface, a medial side connecting the top surface and the bottom surface, and a lateral side distal from the medial side. An anterior side extends between the medial side and the lateral side. The anterior side connects the top surface and the bottom surface. A posterior side extends between the lateral side and the medial side, distal from the anterior side. The top surface is adjustable relative to the bottom surface about two orthogonal axes.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

DETAILED DESCRIPTION

In the drawings, like numerals indicate like elements throughout. Certain terminology is used herein for convenience only and is not to be taken as a limitation on the present invention. For purposes of this description, the terms "anterior", "posterior", "lateral", "medial", "superior" and "inferior" describe the position of surfaces or features relative to the anatomy. The term "anterior" refers to features having a relative position toward the front side of a spine, and "posterior" refers to features having a relative position toward the rear side of the spine. The term "lateral" refers to features having a relative position toward the left or right side of the spine. The term "medial" refers to features having a relative position toward the center of the spine. The term "cranial" refers to features having a relative position above other features, and the term "caudal" refers to features having a relative position below other features. The terminology includes the words specifically mentioned, derivatives thereof and words of similar import.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring to FIGS. 1-6, a wedge implant 100 according to a first exemplary embodiment of the present invention is shown. Wedge implant 100 is inserted into a single vertebra 50 in a spine 52 to readjust the caudal and cranial plans of vertebra 50 to alleviate scoliosis in spine 52. While a single wedge implant 100 is shown being inserted into a single vertebra 50, those skilled in the art will recognize that additional wedge implants 100 can also be inserted into additional vertebrae 50 as needed to alleviate scoliosis.

Figure 1:
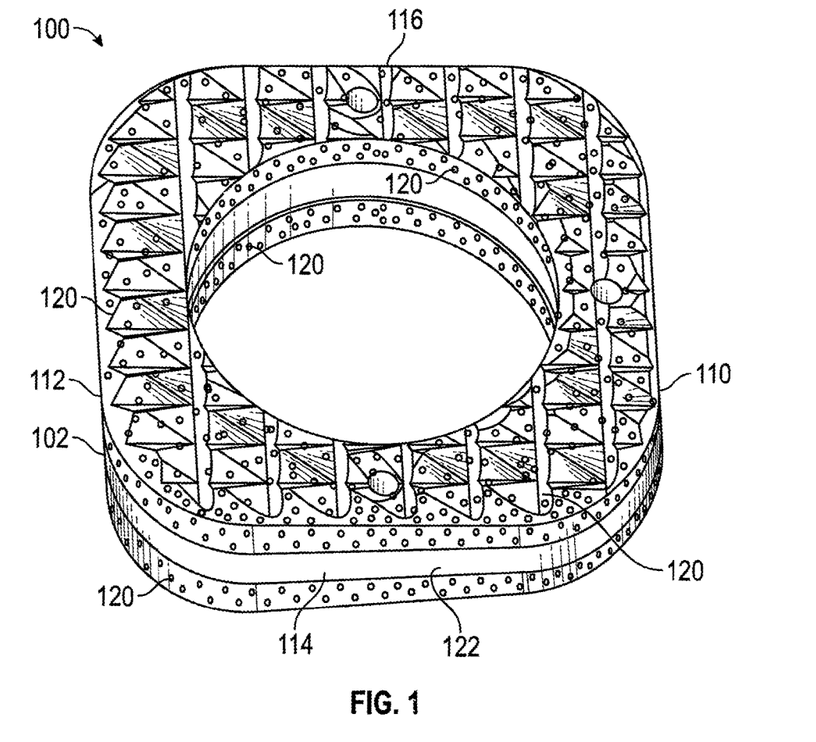
FIG. 1 shows a perspective view of a wedge implant according to a first exemplary embodiment of the present invention.
Figure 2:
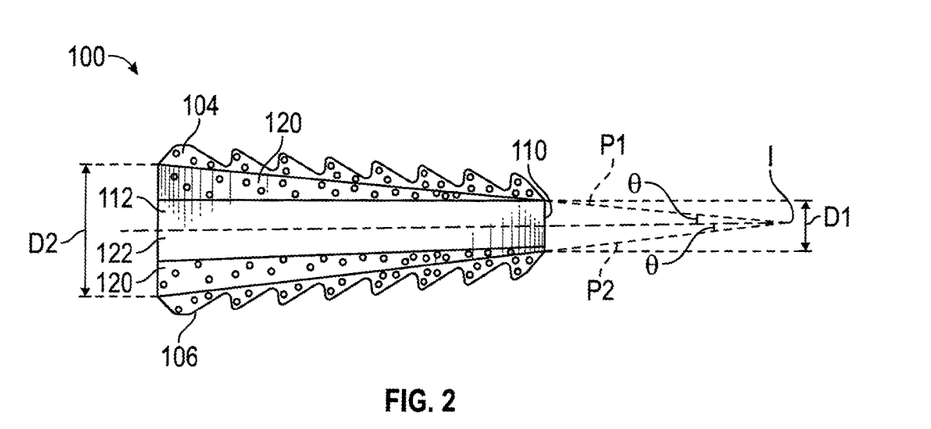
FIG. 2 shows a lateral side elevational view of the wedge implant shown in FIG. 1.
Figure 3:
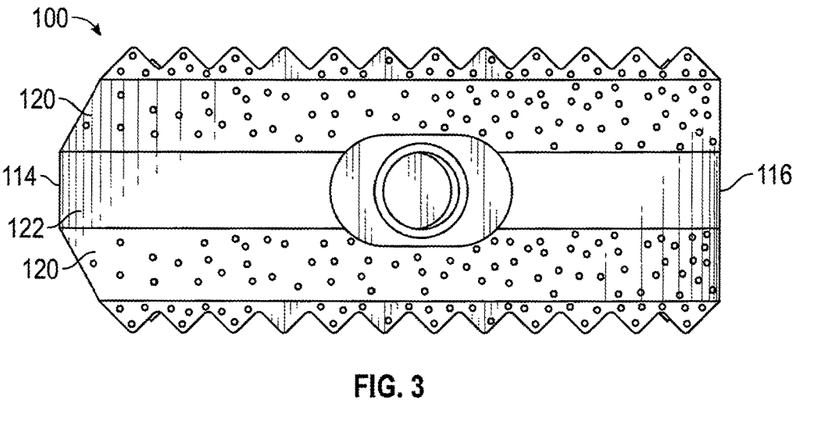
FIG. 3 shows a posterior side elevational view of the wedge implant shown in FIG. 1.

Wedge implant 100 includes an outer perimeter 102 that defines implant 100. Wedge implant 100 also includes a top surface 104 extending generally in a first plane P1 and a bottom surface 106 extending in a second plane P2. Second plane P2 extends obliquely with respect to first plane P1. As shown in FIG. 2, first plane P1 intersects second plane P2 at a location "I" outside outer perimeter 102 of implant 100. Top surface 104 and bottom surface 106 can be planar surfaces. Alternatively, top surface 104 and bottom surface 106 can have other shapes, such as, for example, domed surfaces.

A medial surface 110 extends between top surface 104 and bottom surface 106 proximate to the intersection of first plane P1 and second plane P2. A lateral surface 112 extends between top surface 104 and bottom surface 106 distal from the intersection of first plane P1 and second plane P2. An anterior surface 114 extends a first distance D1 between top surface 102 and bottom surface 104 between medial surface 110 and lateral surface 112. Anterior surface 114 extends generally a constant first distance D1 across its length. A posterior surface 116 extends a second distance D2 between top surface 104 and bottom surface 106 between medial surface 110 and lateral surface 112. Posterior surface 116 extends generally a constant second distance D2 across its length. Second distance D2 is greater than first distance D1.

Figure 7:
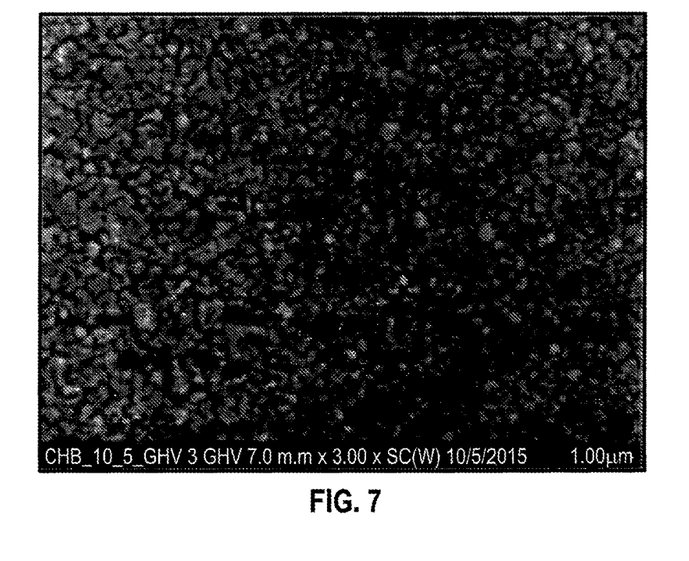
FIG. 7 shows an enlarged view of an osteointegration surface used to coat a portion of the wedge implant shown in FIG. 1.

In an exemplary embodiment, body 102 is constructed from a material having a relatively low stiffness, such as, for example, poly-ether-ether ketone ("PEEK"), which has a modulus of elasticity about 3.6 GPa. In an exemplary embodiment, an antimicrobial and/or osteointegration surface 120, shown in detail in FIG. 7, can be disposed on each of top surface 104 and bottom surface 106. In an exemplary embodiment, the osteointegration portion of surface 120 can be titanium and the antimicrobial portion of surface 120 can be silver or titanium nanotextured or titanium oxide nanostructured.

Osteointegration surface 120 extends downwardly from top surface 104 along medial surface 110, lateral surface 112, anterior surface 114, and posterior surface 116 only a portion of the way to bottom surface 106. Similarly, osteointegration surface 120 can extend upwardly from bottom surface 106 along medial surface 110, lateral surface 112, anterior surface 114, and posterior surface 116 only a portion of the way to top surface 104, resulting in a band 122 around outer perimeter 102 of implant 100 that is free from osteointegration surface 120. In an exemplary embodiment, band 122 has a cranial-to-caudal dimension of about 0.01 mm. Alternatively, band 122 can have a cranial-to-caudal dimension of greater than about 0.1 mm. The existence of band 122 allows for flexing of implant 100, which is softer with a lower modulus of elasticity than osteointegration surface 120, without loading compressive forces onto osteointegration surface 120.

Figure 5:
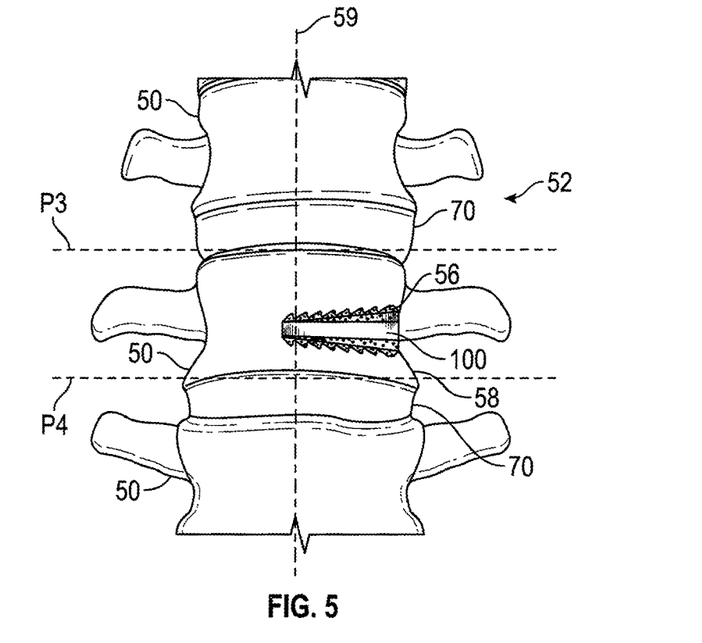
FIG. 5 shows a posterior side elevational view of the wedge implant shown in FIG. 1 inserted into a vertebra a spinal column.

To correct adult or pediatric scoliosis deformity, implant 100 can be inserted into vertebra 50 in a lateral-to-medial direction to realign spine 52 with the craniocaudal axis 59, as shown in FIG. 5. To insert wedge 100, an osteotomy is performed on vertebra 50 by making an incision 56 in vertebra 50. In an exemplary embodiment, the insertion 56 can be made from lateral side 58 of vertebra 50 inwardly toward the center of vertebra 50, and inserting implant 100 into incision 56. Alternatively, incision 56 may be made to the contralateral side of vertebra 50, with implant 100 being inserted therein. In pediatric patients, the osteotomy is formed in a way not violate the growth plate of vertebra 50. This insertion effectively pivots cranial plane P3 relative to caudal plane P4 of vertebra 50 in an effort to make cranial plane P3 and caudal plane P4 closer to match the crainocaudal axis of spine 52 and aligned in the sagittal plane.

Figure 4:
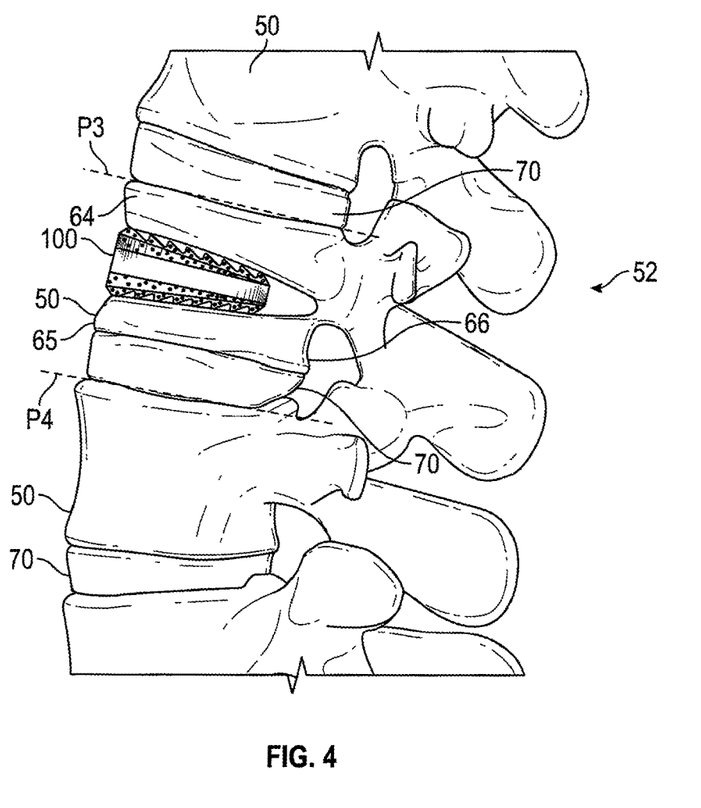
FIG. 4 shows a lateral side elevational view of the wedge implant shown in FIG. 1 inserted into a vertebra in a spinal column.

Similarly, to correct adult or pediatric scoliosis deformity, implant 100 can be inserted into vertebra 50 in a anterior-to-posterior direction to restore lordosis or kyphosis of the spine, as shown in FIG. 4. To insert wedge 100, an osteotomy is performed on vertebra 50 by making an incision 64 in vertebra 50 from posterior side 65 of vertebra 50 inwardly toward anterior side 66 of vertebra 50, and inserting implant 100 into incision 64. This insertion effectively pivots cranial plane P3 relative to caudal plane P4 in an effort to make cranial plane P3 and caudal plane P4 closer to normal conditions to restore lordotic or kyphotic angulation the spine 52.

Figure 6:
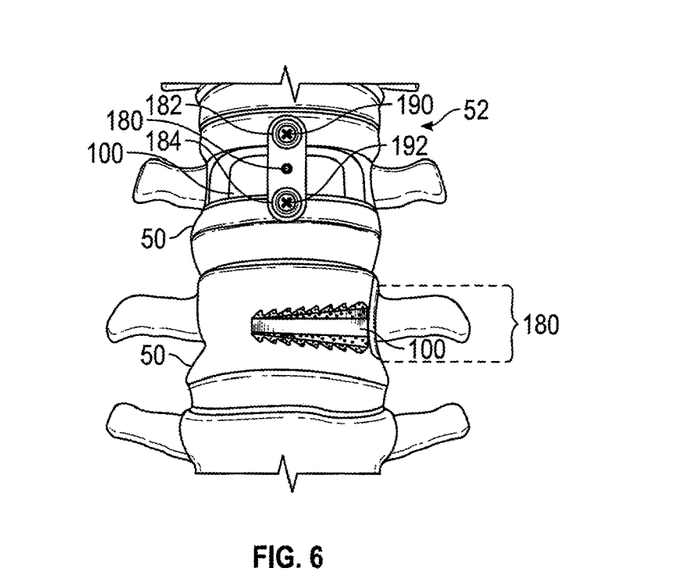
FIG. 6 shows a retaining plate used to retain the wedge implant shown in FIG. 1 in the vertebrae shown in FIGS. 4 and 5.

In either of the above two procedures, a retaining plate 180 is fixed to vertebra 50 to secure implant 100 to vertebra 50. FIG. 6 shows retaining plate 180 being used to secure implant 100 inserted in the posterior-to-anterior direction in top vertebra 50, and retaining plate 180 used to secure implant 100 inserted in the lateral-to-medial direction. The retaining plate 180 is shown in both anterior-posterior and medial-lateral alignment. However a surgeon will generally only insert retaining plate 180 from one direction in vertebra 50 or adjacent vertebrae 50.

Retaining plate 180 is an elongate member with a first hole 182 at a first end 184 thereof and a second hole 186 at a second end 188 thereof. A first screw 190 is inserted through first hole 182 and into vertebra 50 toward or parallel with cranial plane P3, while a second screw 192 is inserted through second hole 186 and into vertebra 50 toward parallel with caudal plane P4. In an exemplary embodiment, retaining plate 180 and screws 190, 192 can be made from standard biomaterials, such as titanium, or bio-resorbable materials, such as, for example, magnesium-based alloys that will ultimately dissolve by the time implant 100 has been fully engaged by vertebra 50.

Figure 6A:
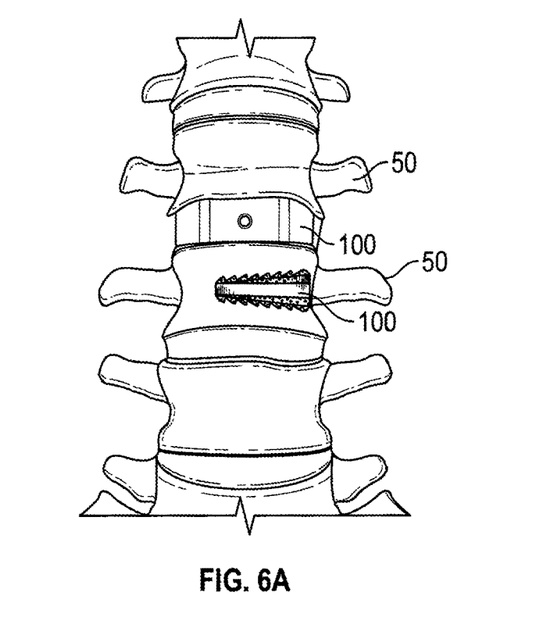
FIG. 6A shows a lateral side elevational view of the wedge implant shown in FIG. 1 inserted between adjacent vertebrae in a spinal column.

While an exemplary use of implant 100 as described above is used in a single vertebra 50, those skilled in the art will recognize that in some cases, it may be more advantageous to remove a disk 70 between two adjacent vertebrae 50 and insert implant 100 between the two adjacent vertebrae 50, as an interbody implant, as shown in FIG. 6A. In such a case, screw 190 for plate 180 can be secured into the upper vertebra 50 and screw 192 for plate 180 can be secured into the lower vertebra 50.

In an exemplary embodiment, it may be necessary to remove at least a lower portion of the upper vertebra 50 and an upper portion of the lower vertebra 50 in order to properly insert implant 100.

Figure 8:
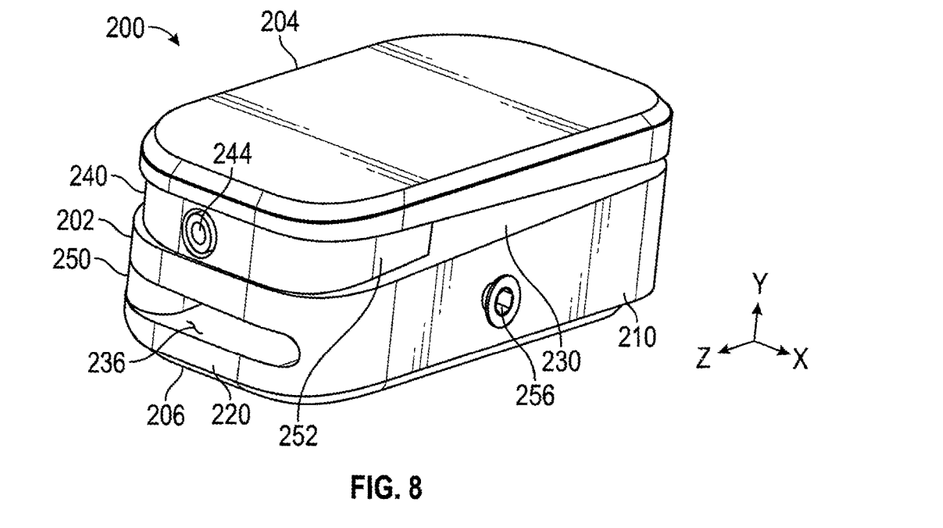
FIG. 8 shows a perspective view of a wedge implant assembly according to a second exemplary embodiment of the present invention.
Figure 9:
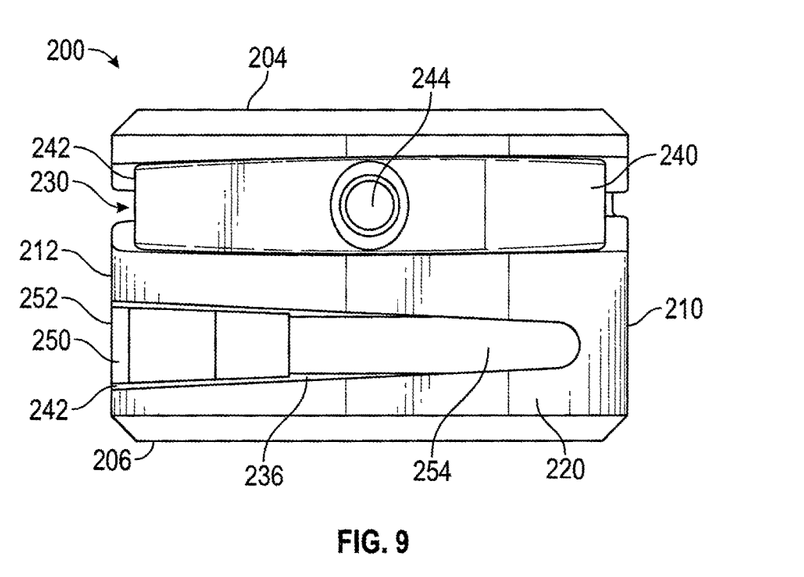
FIG. 9 shows a lateral elevational view of the wedge implant assembly shown in FIG. 8.
Figure 10:
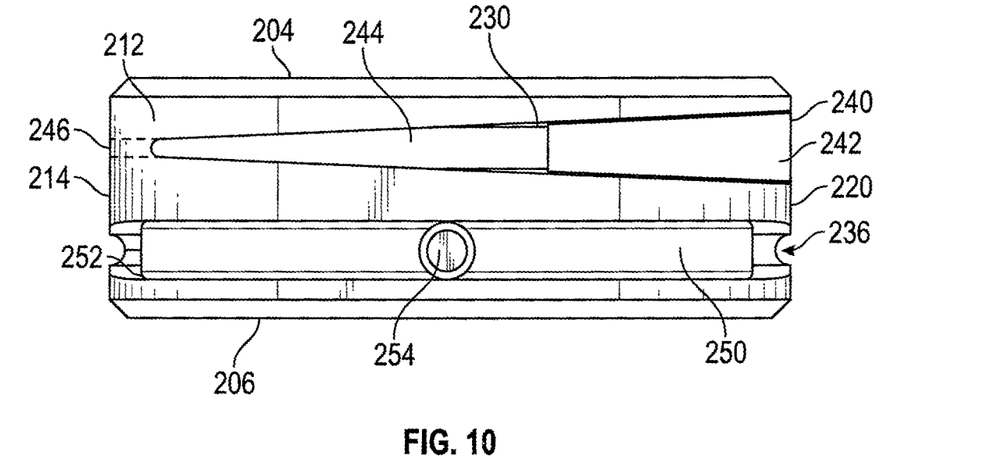
FIG. 10 shows a posterior elevational view of the wedge implant assembly shown in FIG. 8.

In an alternative embodiment, referring to FIGS. 8-10, a bi-planar adjustable implant 200 according to an exemplary embodiment of the present invention is shown. Implant 200 can be inserted into an osteotomy in vertebra 50 as discussed above with respect to implant 100. Alternatively, as also discussed above with respect to implant 100, upon removal of a disk between two adjacent vertebrae 50, implant 200 can be inserted into the space between the two vertebrae 50.

Implant 200 includes a body 202 having a top surface 204 and a bottom surface 206, distal from top surface 204. Top surface 204 and bottom surface 206 can be planar surfaces. Alternatively, top surface 204 and bottom surface 206 can have other shapes, such as, for example, domed surfaces.

A medial side 214 connects top surface 204 and bottom surface 206. A lateral side 220 is located distal from medial side 214. An anterior side 210 extends between medial side 214 and lateral side 220 such that anterior side 210 connects top surface 204 and bottom surface 206 to each other. A posterior side 212 extends between lateral side 220 and medial side 214, distal from anterior side 210.

Implant 200 has a first slot 230 extending from lateral side 220 toward medial side 214 and a second slot 236 extending from posterior side 220 toward anterior side 214. Slots 230, 236 allow for the insertion of wedges to alter the angle of the plane of top surface 204 with respect to bottom surface 206. The location of slot 230 relative to slot 236 allows for the adjustment of top surface 204 relative to bottom surface 206 about two axes, namely, the x and z axes as shown in FIG. 8.

A first wedge assembly 240 is inserted into first slot 230. As used herein, the term "wedge assembly" means any device, inserted in an implant, that can be manipulated to change the angle of at least one face of the implant. First wedge assembly 240 has a first member 242 translatable in a lateral-to-medial direction. In an exemplary embodiment, first member 242 is a wedge having a tapered profile from the lateral direction to the medial direction as shown in FIG. 9. A second member 244 is operatively connected to first member 242 such that operation of second member 244 translates first member 240 in the lateral-to-medial direction. In an exemplary embodiment, second member 244 can be a screw threadedly inserted through first member 242, such that rotation of second member 244 about the "Z" axis translates first member 242 in the "Z" direction. Second member 244 can include an adjusting mechanism 246, such as, for example, a screw head, extending from anterior side 214.

Similarly, a second wedge assembly 250 is inserted into second slot 236. Second wedge assembly 250 has a first member 252 translatable in a posterior-to-anterior direction. Similar to first wedge assembly 240, first member 252 is a wedge having a tapered profile from the lateral direction to the medial direction as shown in FIG. 10. A second member 254 is operatively connected to first member 252 such that operation of second member 254 translates first member 250 in the posterior-to-anterior direction. In an exemplary embodiment, second member 254 can also be a screw threadedly inserted through first member 252, such that rotation of second member 254 about the "X" axis translates second member 252 in the "X" direction. Second member 254 can include an adjusting mechanism 256, such as, for example, a screw head, extending from anterior side 210.

Translation of first member 242 of first wedge assembly 240 pivots top surface 204 with respect to bottom surface 206 about medial side 214 and translation of first member 252 of second wedge assembly 250 pivots top surface 204 with respect to bottom surface 206 about anterior side 210.

Figure 11:
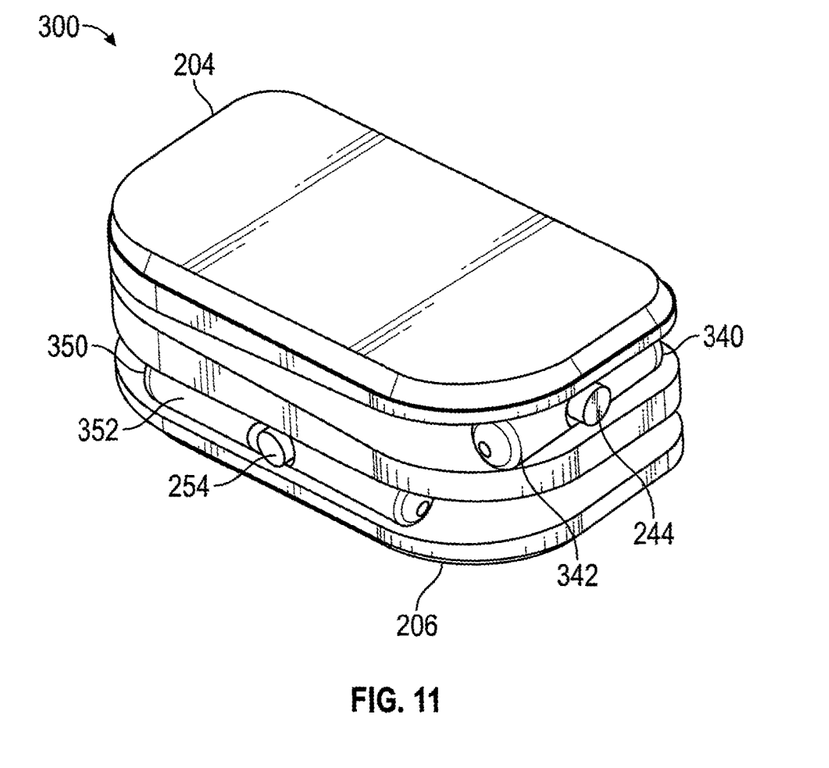
FIG. 11 shows a perspective view of a wedge implant assembly according to a third exemplary embodiment of the present invention.
Figure 12:
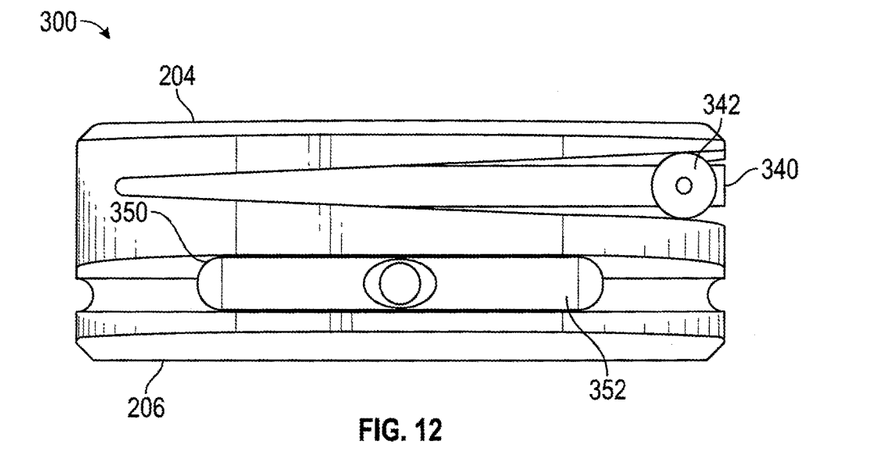
FIG. 12 shows a posterior elevational view of the wedge implant assembly shown in FIG. 11.
Figure 13:
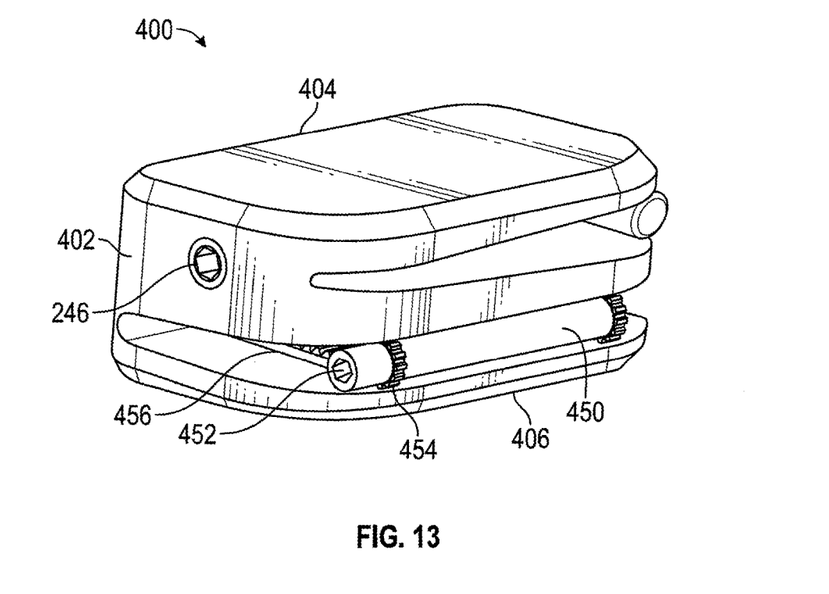
FIG. 13 shows a perspective view of a wedge implant assembly according to a fourth exemplary embodiment of the present invention.
Figure 14:
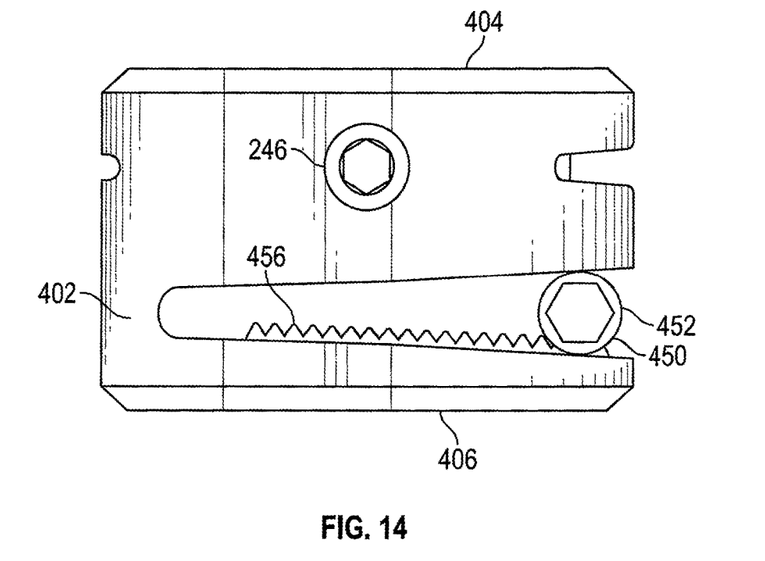
FIG. 14 shows a medial side elevational view of the wedge implant assembly shown in FIG. 13.
Figure 15:
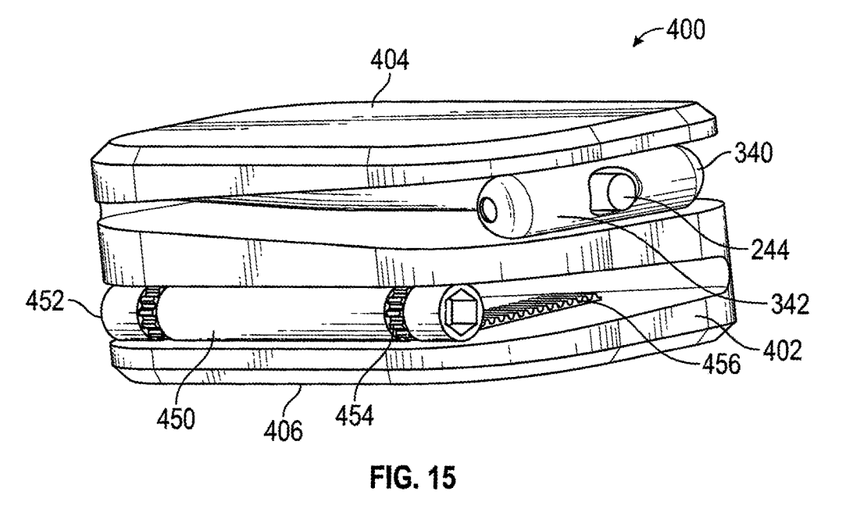
FIG. 15 shows a rear perspective view of the wedge implant assembly shown in FIG. 13.
Figure 16:
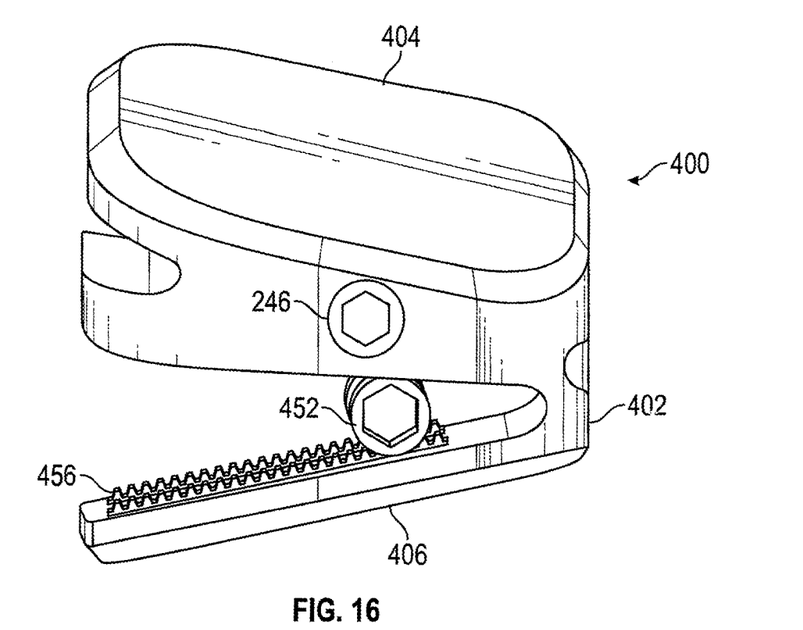
FIG. 16 shows a lateral side elevational view of the wedge implant assembly shown in FIG. 15.
Figure 17:
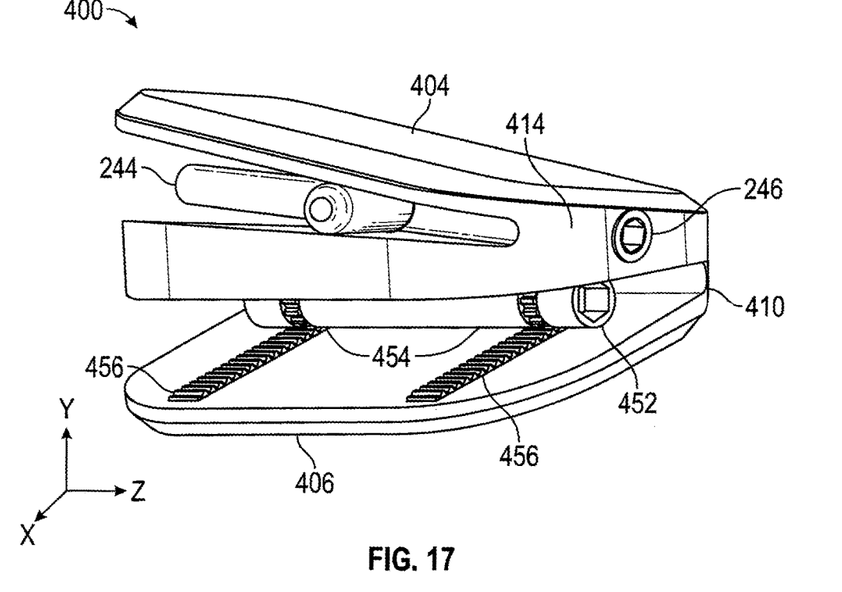
FIG. 17 shows a rear perspective view of the wedge implant assembly shown in FIG. 15, with a second wedge assembly actuated to adjust the tilt angle of the top surface of the wedge implant assembly.

In an alternative exemplary embodiment of a wedge assembly 300, shown in FIGS. 11 and 12, instead of the wedge provided as first member 242 and 252, wedge assemblies 340, 350 utilize a cylinder 342, 352. Second member 244, 254 from wedge assembly 200 can be used to activate cylinder 342, 352, respectively. It is noted, however, that, for either wedge assembly 200 or wedge assembly 300, first wedge assembly 240 is actuated from lateral side 220 while second wedge assembly 250 is actuated from posterior side 212. It is desired to be able to actuate both first wedge assembly 240 and second wedge assembly 250 from the same side in order to minimize incisions made into the patient. Therefore, if wedge assembly 200, 300 is inserted from the lateral side of vertebra 50, it is desired to be able to actuate first wedge assembly 240 and second wedge assembly 250 from the lateral side of vertebra 50. Therefore, to actuate second wedge assembly, it may be desired to use a driver (not shown) having a right angle drive.

An alternative embodiment of an implant assembly 400 according to the present invention is shown in FIGS. 13-17. Implant assembly 400 is similar to implant assembly 300, with the exception of, instead of second wedge assembly 350, a second wedge assembly 450 is provided. Second wedge assembly 450 includes a first member 452, which is a cylinder having a plurality of gear teeth 454 formed around an exterior perimeter thereof. Second wedge assembly 450 includes a second member fixedly 456 connected to body 402 of implant assembly 400. In an exemplary embodiment, second member 456 is a toothed rack engageable with gear teeth 454 of first member 452 such that, when first member 452 is rotated, gear teeth 454 translates first member 452 along second member 456. An exemplary embodiment, as shown FIG. 17, two sets of gear teeth 454 are formed on first member 452 and two sets of toothed racks of second member 456 are connected to body 402, although those skilled in the art will recognize that more or less than two sets can be used.

An advantage of implant assembly 400 is that first member 342. A first wedge assembly 340, and first member 452 of second wedge assembly 450 can both be actuated from the same side of the patient, such as, for example, the lateral side.

Translation of first member 342 of first wedge assembly 340 pivots top surface 404 with respect to bottom surface 406 about medial side 414 and translation of first member 252 of second wedge assembly 250 pivots top surface 204 with respect to bottom surface 206 about anterior side 410.

Figure 18:
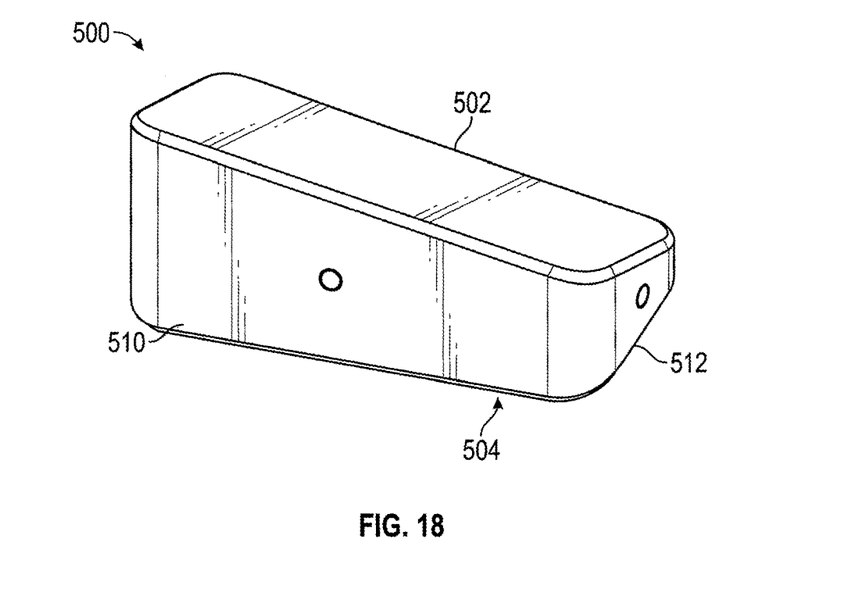
FIG. 18 shows a perspective view of a wedge implant assembly according to a fifth exemplary embodiment of the present invention.
Figure 19:
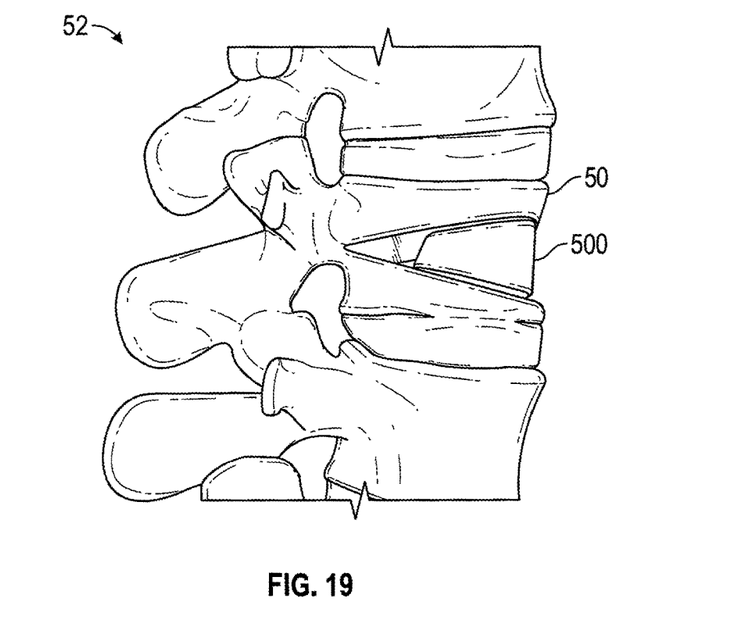
FIG. 19 shows a right side elevational view of the wedge implant assembly shown in FIG. 18 inserted into a vertebra of a patient.
Figure 20:
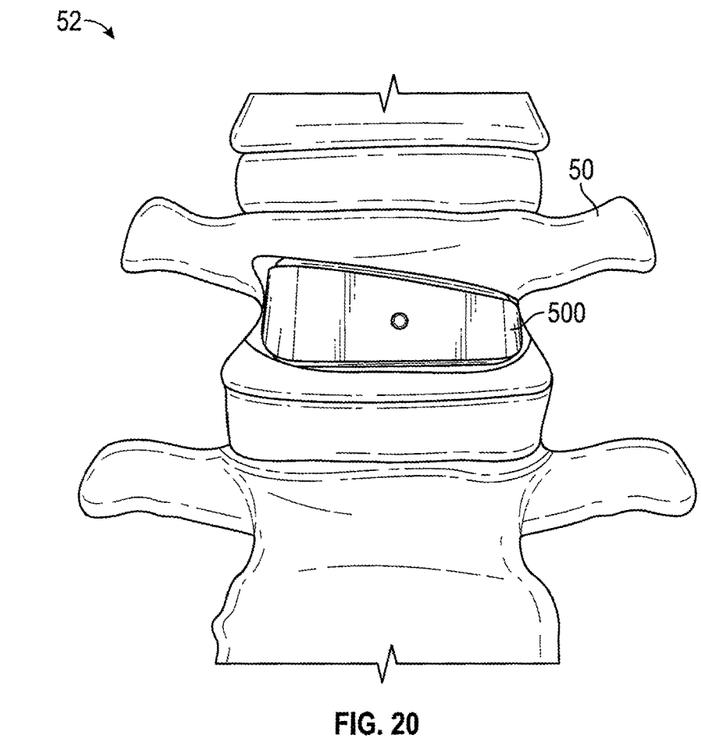
FIG. 20 shows a posterior side elevational view of the wedge implant assembly and vertebra shown in FIG. 19.
Figure 21:
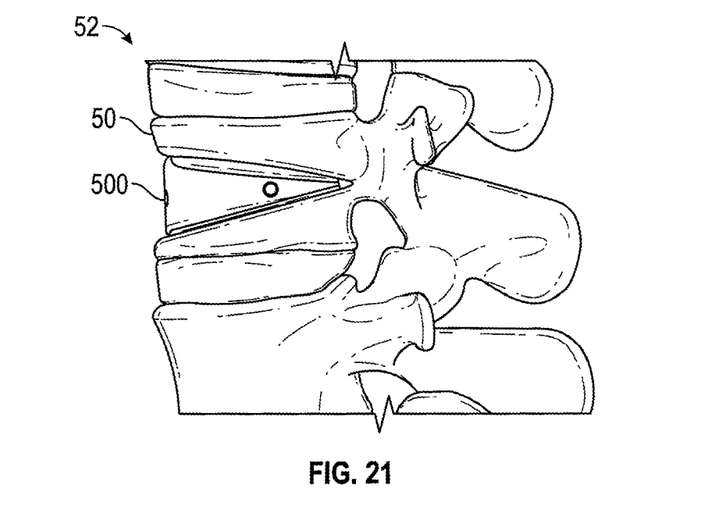
FIG. 21 shows a left side elevational view of the wedge implant assembly, and vertebra shown in FIG. 19.

Also, similar to wedge implant 100, wedge implant assembly 200, 300, 400 can include an antimicrobial and/or osteointegration surface disposed on top and bottom surfaces thereof, with only a portion of each of the medial side, the lateral side, the anterior side, and the posterior side, including the osteointegration surface disposed thereon. An alternative embodiment of an implant assembly 500 according to the present invention is shown in FIGS. 18-22. Implant assembly 500 is a non-adjustable bi-planar wedge. Wedge 500 is similar to wedge 100, but, instead of anterior surface 114 extending generally a constant first distance D1 across its length and posterior surface 116 extending generally a constant second distance D2 across its length, as shown in FIG. 18, at least two adjacent surfaces taper from larger to smaller, forming a bi-planar top surface 502.

By way of example only, posterior surface 510 tapers from larger to smaller in a left-to-right direction and lateral surface 512 tapers from larger to smaller in a posterior-to-anterior direction, resulting in wedge assembly 500 that can be implanted into vertebra 50, as shown in FIGS. 19-22. An advantage of wedge assembly 500 is that wedge assembly 500 can be used to simultaneously correct a spinal column 52 that has abnormal curvature into the lateral-to-medial direction as well as in the posterior-to-anterior direction. Optionally, although not shown, a retaining plate 180 can be used to secure wedge assembly 500 in vertebra 50.

Figure 22:
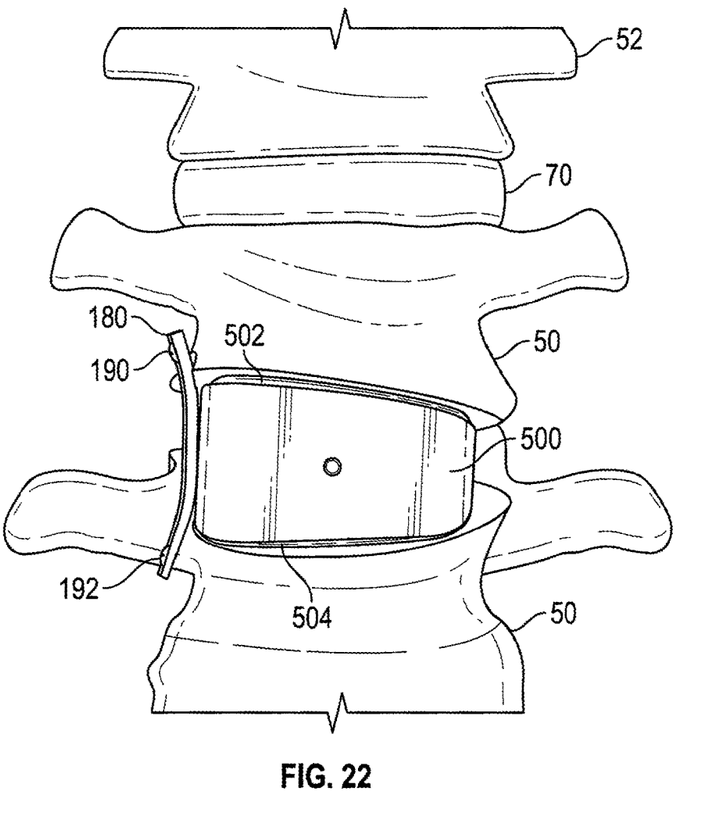
FIG. 22 shows a posterior side elevational view of the wedge implant assembly shown in FIG. 18, inserted between two adjacent vertebrae.

FIG. 22 shows wedge assembly 500 inserted between two adjacent vertebrae 50 with a disk, similar to disc 70 previously disposed between the adjacent vertebrae 50, having been removed and wedge assembly 500 inserted therein. Optionally, plate 180 can be used to secure wedge assembly 500 between the adjacent vertebrae 50 using screw 190 to secured plate 180 to the upper vertebra 50 and screw 192 to secure plate 180 to the lower vertebra 50. As shown FIG. 22, plate 180 is attached to a lateral side of spine 52. Those skilled in the art, however, will recognize that plate 180 can also be attached to spine 152 along the posterior side of spine 52.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A wedge adapted for insertion into a monolithic bone, the wedge having an outer perimeter, the wedge comprising:
    (a) a top surface extending generally in a first plane, the top surface comprising an osteointegration surface disposed thereon;
    (b) a bottom surface extending in a second plane, the second plane extending obliquely with respect to the first plane, the first plane intersecting the second plane outside the outer perimeter of the implant and comprising an osteointegration surface disposed thereon;
    (c) a medial surface extending between the top surface and the bottom surface proximate to the intersection of the first plane and the second plane;
    (d) a lateral surface extending between the top surface and the bottom surface distal from the intersection of the first plane and the second plane;
    (e) an anterior surface extending a first distance between the top surface and the bottom surface between the medial surface and the lateral surface; and
    (f) a posterior surface extending a second distance between the top surface and the bottom surface between the medial surface and the lateral surface, the second distance being greater than the first distance, wherein the osteointegration surface extends upwardly from the bottom surface along the medial surface, the lateral surface, the anterior surface, and the posterior surface only a portion of the way to the top surface.

2. The wedge according to claim 1, wherein the osteointegration surface extends downwardly from the top surface along the medial surface, the lateral surface, the anterior surface, and the posterior surface only a portion of the way to the bottom surface.

3. A wedge adapted for insertion into a monolithic bone, the wedge comprising:
    (a) a posterior surface tapering from larger to smaller in a left-to-right direction;
    (b) a lateral surface adjacent to the posterior surface, the lateral surface tapering from larger to smaller in a posterior-to-anterior direction;
    (c) a top surface connected to each of the posterior surface and the lateral surface, the top surface comprising at least one of an antimicrobial surface and osteointegration surface;
    (d) a bottom surface connected to each of the posterior surface and the lateral surface, the bottom surface comprising at least one of an antimicrobial surface and an osteointegration surface;
    (e) a medial surface extending between the top surface and the bottom surface, distal from the lateral surface; and
    (f) an interior surface extending between the top surface and the bottom surface, distal from the posterior surface,
    wherein the osteointegration surface extends downwardly from the top surface along the medial surface, the lateral surface, the anterior surface, and the posterior surface only a portion of the way to the bottom surface;
    wherein the top surface extends along the posterior surface in a first line and the bottom surface extends along the posterior surface in a second line, oblique to the first line; and
    wherein the top surface extends along the lateral surface in a third line and the bottom surface extends along the lateral surface in a fourth line, oblique to the third line.

4. The wedge according to claim 3, wherein the first line extends oblique to the third line.

5. The wedge according to claim 4, wherein the second line extends co-planar to the fourth line.

6. The wedge according to claim 3, wherein the top surface is bi-planar with respect to the bottom surface.

7. The wedge according to claim 3, wherein the osteointegration surface extends upwardly from the bottom surface along the medial surface, the lateral surface, the anterior surface, and the posterior surface only a portion of the way to the top surface.

8. A wedge adapted for insertion into a monolithic bone, the wedge comprising:
    (a) a top surface extending in a first plane, the top surface comprising at least one of an antimicrobial surface and an osteointegration surface;
    (b) a bottom surface extending in a second plane, the bottom surface comprising at least one of an antimicrobial surface and an osteointegration surface;
    (c) a posterior surface connecting the top surface and the bottom surface;
    (d) a lateral surface adjacent to the posterior surface and connecting the top surface and the bottom surface;
    (e) an anterior surface adjacent to the lateral surface and connecting the top surface and the bottom surface; and
    (f) a medial surface adjacent to the anterior surface and the posterior surface and connecting the top surface and the bottom surface;
    wherein an intersection between the medial surface and the lateral surface forms a first distance between the top surface and the bottom surface;
    wherein an intersection between the posterior surface and the lateral surface forms a second distance between the top surface and the bottom surface, less than the first distance;
    wherein an intersection between the lateral surface and the anterior surface forms a third distance between the top surface and the bottom surface, less than the second distance; and
    wherein the osteointegration surface extends downwardly from the top surface along the medial surface, the lateral surface, the anterior surface, and the posterior surface only a portion of the way to the bottom surface.

9. The wedge according to claim 8, wherein an intersection between the medial surface and the anterior surface forms a fourth distance between the top surface and the bottom surface, greater than the first distance.

10. The wedge according to claim 8, wherein the osteointegration surface extends upwardly from the bottom surface along the medial surface, the lateral surface, the anterior surface, and the posterior surface only a portion of the way to the top surface.

* * * * *